United States Patent
May (10) Patent No.: US 7,420,172 B2
(45) Date of Patent: Sep. 2, 2008

(54) SYSTEM AND METHOD FOR MEASURING WATER VAPOR IN NATURAL GAS

(75) Inventor: Randy D. May, Wilmington, NC (US)

(73) Assignee: Analytical Specialties, Inc., Houston, TX (US)

( * ) Notice: Subject to any disclaimer, the term of this patent is extended or adjusted under 35 U.S.C. 154(b) by 0 days.

(21) Appl. No.: 11/986,893

(22) Filed: Nov. 27, 2007

(65) Prior Publication Data

US 2008/0135760 A1  Jun. 12, 2008

Related U.S. Application Data

(60) Provisional application No. 60/873,122, filed on Dec. 6, 2006.

(51) Int. Cl.
*G01J 5/58* (2006.01)
(52) U.S. Cl. ....................................................... 250/343
(58) Field of Classification Search ................... 250/343
See application file for complete search history.

(56) References Cited

U.S. PATENT DOCUMENTS

| 6,657,198 | B1 | 12/2003 | May |
| 7,132,661 | B2 | 11/2006 | May |
| 2006/0123884 | A1* | 6/2006 | Selker et al. ............... 73/24.02 |
| 2007/0058686 | A1* | 3/2007 | Capasso et al. .......... 372/43.01 |

* cited by examiner

*Primary Examiner*—David P. Porta
*Assistant Examiner*—Marcus H. Taningco
(74) *Attorney, Agent, or Firm*—MacCord Mason PLLC

(57) ABSTRACT

The amount of water vapor in natural gas at different levels, including at levels below 10 ppmv, is measured by directing a light from a quantum cascade laser at a frequency in the 5.01 to 5.03 micron or the 5.07 to 50.9 micron wavelength range through natural gas containing water vapor. A detector is configured to detect the intensity of light transmitted through the natural gas from the laser; and an analyzer is coupled to the detector for determining the level of water vapor in the natural gas.

10 Claims, 9 Drawing Sheets

SYSTEM AND METHOD FOR MEASURING WATER VAPOR IN NATURAL GAS

The application claims the benefit of the filing date of U.S. Provisional Application Ser. No. 60/873,122, entitled System and Method For Measuring Water Vapor In Natural Gas, filed Dec. 6, 2006.

BACKGROUND OF THE INVENTION (1) Field of the Invention

The present invention relates generally to a system and method for measuring low amounts of water in natural gas, and in particular to the use of a single-mode laser, e.g., a quantum cascade laser, emitting light in the 5.01 to 5.03 micron wavelength range, and less preferably in the 5.07 to 5.09 micron wavelength range, capable of measuring water vapor at below 10 ppmv. While the system and method is distinguishable from prior art systems and methods in the capability to measure at these lower volumes, it will be understood that the system and method may also be used to measure water vapor at above 10 ppmv.

(2) Description of the Prior Art

Distribution of commercial natural gas (consisting primarily of methane, $CH_4$), requires an extensive network of pipelines through which the gas flows under pressure. Depending on many factors, the gas stream can also contain varying levels of other components such as heavier hydrocarbons, carbon dioxide ($CO_2$) and water ($H_2O$), among others. Due to the physical size and extent of the distribution pipeline system, custody of the gas can change hands many times between the point of origin and the end customer (typically a municipal utility serving individual homes and businesses). Pipeline networks are owned and managed by dozens of companies in the U.S. (and a similar situation exists anywhere in the world where natural gas is produced and used), and extensive monitoring of the gas quality is performed at most custody transfer points (i.e. the point at which ownership of the pipeline section(s) changes).

In addition to measurements of basic gas quality, it is a requirement to also monitor for levels of certain gases for safety and pipeline integrity reasons. Each of these gases has certain tariff levels which cannot be exceeded. For example, levels of hydrogen cyanide ($H_2S$) cannot exceed 4 parts per million by volume (ppmv) as it is a highly toxic gas (less toxic mercaptons are added to natural gas to create the "rotten egg" smell so that leaks inside a building can be detected by smell). Levels of $H_2O$ and $CO_2$ are also controlled because these gases can corrode the interior of the high pressure pipelines either directly, or by forming acids which attack the interior pipeline walls. $H_2O$ levels, in particular, must be kept low (typically below 150 ppmv in mid latitude locations, and much lower in colder northern climates) to minimize corrosion potential. Therefore, all natural gas pipeline operators are required to perform continuous measurements of the water vapor content within their pipelines.

$H_2O$ is a difficult gas to measure within a natural gas mixture using conventional humidity or moisture monitoring techniques. Most of these sensors are in direct contact with the natural gas stream, and the small levels of contaminates in the natural gas eventually alter the characteristics of the sensor causing it to either fail, or drift unacceptably out of calibration. Therefore, maintenance costs are high and the sensors are unreliable.

In 1999 SpectraSensors, Inc. (San Dimas, Calif.) developed the first laser-based $H_2O$ sensors for natural gas which offered a reliable and accurate solution to the problem of $H_2O$ monitoring in natural gas for mid-latitude locations where $H_2O$ levels cannot exceed 150 ppmv, and lower detection limits are typically 5-10 ppmv. U.S. Pat. No. 6,657,198, issued Dec. 2, 2003, by the present inventor, describes and claims a system for detecting water vapor in natural gas that is comprised of a light source emitting light at a frequency substantially corresponding to an absorption line of water in the 1.877-1.901 .mu.m wavelength range, wherein said light source is positioned to absorb light through the natural gas; a detector configured to detect the intensity of light emitted from the light source; and electronics coupled to the detector for determining the level of water vapor in the natural gas.

U.S. Pat. No. 7,132,661, issued Nov. 7, 2006, also by the present inventor, describes and claims a system comprised of at least one chemical sensor to detect a level of water vapor in natural gas; at least one optical sensor to detect a level of water vapor in natural gas, the optical sensor comprising: a light source emitting light at substantially a single wavelength having a width sufficiently narrow to conduct single line spectroscopy and corresponding to a single absorption line at which water molecules absorb light at a substantially greater level than natural gas molecules; a detector configured to detect the intensity of light emitted from the light source; electronics coupled to the detector for determining the level of water vapor in the natural gas using single line harmonic spectroscopy; and a supply line delivering natural gas to the at least one chemical sensor and the at least one optical sensor for parallel measurements.

The '661 patent claims three specific wavelength regions where $H_2O$ could be monitored within a background of primarily $CH_4$ (natural gas consists of 85-98% $CH_4$). These wavelength regions (near 0.95 microns, 1.9 microns, and 2.7 microns) meet the need for mid-latitude tariff levels for $H_2O$ monitoring (i.e., below 150 ppmv). However, there are many locations in the U.S., Canada and other regions worldwide where it is necessary to monitor $H_2O$ at levels well below 10 ppmv.

Molecular absorption spectra consist of broad features called "bands." Each band, in turn, is composed of up to thousands of individual closely-spaced "lines" that can only be observed with a high resolution spectrometer. Lines have no substructure, so if the resolution of the light source is sufficient to observe a single line without distortion, it is possible to separate an $H_2O$ line from a $CH_4$ line in a gas mixture which contains both gases. The trick then is to locate an $H_2O$ line that is separated sufficiently from the neighboring $CH_4$ lines so that it can be isolated and monitored.

Molecular spectroscopy involves the detection of specific molecules using their unique absorption spectrum, and related studies of the physics behind such light absorption. This technique has been utilized for over 100 years to monitor gases, and "resolution" is a key concept to understand when comparing various approaches to molecular spectroscopy, and in particular why lasers offer many advantages over more conventional techniques. In all molecular spectroscopy methods, a light source is directed through the sample gas of interest to impinge on a detector. As the light passes through the gas sample, certain wavelengths may be absorbed while others pass through, with each gas producing a unique pattern (spectrum) when the detector signal is analyzed as a function of the wavelength of the light source.

In order to "split" the wavelength of a conventional light source (e.g. the sun, a hot filament, etc.) into components it is necessary to use a dispersive element such as a grating. This is analogous to how a prism separates sunlight into visible colors, but instead of a few colors that the human eye can easily see in the prism rainbow, a grating may split the light into hundreds or even thousands of closely-separated wavelengths. The more wavelengths that can be distinguished, the higher the "resolution" of the system, and gratings can produce this wavelength separation throughout the electromagnetic spectrum (visible, infrared, etc.). In this case the light source itself produces a wide, continuous range of wavelengths, and the dispersive element separates that light into many equally-spaced wavelengths. Similar to the teeth on a comb, the higher the resolution the more teeth on the comb, and the more closely they are spaced. The total width of the comb represents the total wavelength region covered by the light source. A low resolution spectrometer (an instrument that measures a molecular absorption spectrum) would have only a few big teeth on the comb, while a high resolution spectrometer would have many closely spaced teeth on the comb. The higher the resolution of the spectrometer, the greater the ability to separate the absorption spectrum into its fine details. Conventional spectrometers have a limit to how many teeth can be created on the comb analogy, but lasers do not.

When the laser was invented in the 1960s, it changed molecular spectroscopy in a major way because it was finally possible to record an absorption spectrum with "infinite" resolution. The spectral purity of the laser output (i.e., one and only one very precise wavelength) eliminates the need for a grating or dispersive element, and there are many laser sources which are continuously tunable over certain wavelength intervals. This means that the single, pure wavelength that the laser outputs can be smoothly tuned over a small wavelength interval. Such lasers are called continuous wave (CW), tunable, single-mode lasers.

While the systems and methods described in the foregoing patents are useful in measuring water levels at higher and mid-levels, there is a continuing need for a simple and effective system and method that would be useful in the measurement of water levels at below 10 ppmv.

SUMMARY OF THE INVENTION

The present invention relates to a system and method for detecting and measuring water vapor in natural gas, and in particular to the monitoring of $H_2O$ at levels below 10 ppmv using high-resolution molecular spectroscopy and a single-mode laser, such as the newly available quantum cascade laser. While the invention will be described with specific reference to quantum cascade lasers, it will be understood that other single-mode lasers operating at the wavelengths described herein, when commercially available, are also encompassed by the present invention. Specifically, it has been found that wavelengths in the 5.01 to 5.03 micron wavelength range, and in particular a specific wavelength, 5.0203 microns, equal to 1991.9 $cm^{-1}$, is ideal for measuring $H_2O$ in natural gas at sensitivity levels greater than is possible using shorter wavelength lasers of the type described and claimed in the above SprectraSensors patents, i.e., natural gas at levels as low as 0.1 ppmv. It has also been found that the amount of $H_2O$ can be measured in the 5.07 to 5.09 micron wavelength range, and in particular at the 5.08 microns wavelength, equal to 1967.5 $cm^{-1}$, but at a lesser sensitivity than in the 5.01 to 5.03 micron wavelength range.

Measurement of these longer wavelength regions, and thereby the more sensitive measurement of $H_2O$ in natural gas, is made possible by the availability of a new type of lasers called quantum cascade (QC) lasers which operate at wavelengths between 4.3 microns and 17 microns. This so-called "fingerprint" region is where most molecules absorb light very strongly in unique patterns. These patterns are called the absorption spectrum, and have been used for decades to monitor gases, liquid and solids for their component elements. QC lasers which operate at near room temperatures (0° C. and above), are now produced by Alpes Lasers in Switzerland and Maxion Technologies in the U.S. Room temperature operation enabling $H_2O$ to be measured in natural gas at the above wavelengths with greater sensitivity is a requirement for an industrial sensor since it is not practical to use liquid cryogens to cool the laser in such applications.

The present system for detecting water vapor in natural gas is therefore comprised of a quantum cascade laser positioned to emit a light beam with wavelengths in the 5.01 to 5.03 micron range or 5.07 to 5.09 micron wavelength range through a body of natural gas, a detector configured to receive light from the laser, and an analyzer coupled to the detector for computing the level of water vapor in the natural gas based on the amount of light detected by the detector. The method for determining the level of water vapor in natural gas comprises: providing a quantum cascade laser positioned to emit a light beam with wavelengths in the 5.01 to 5.03 micron range or the 5.07 to 5.09 micron wavelength range, positioning a detector opposite the laser to detect the level of emitted light transmitted through the natural gas, supplying a sample of natural gas between the laser and the detector, and determining the concentration of water vapor in the natural gas based on the level of light detected by the detector.

DETAILED DESCRIPTION OF THE INVENTION

Figure 1:
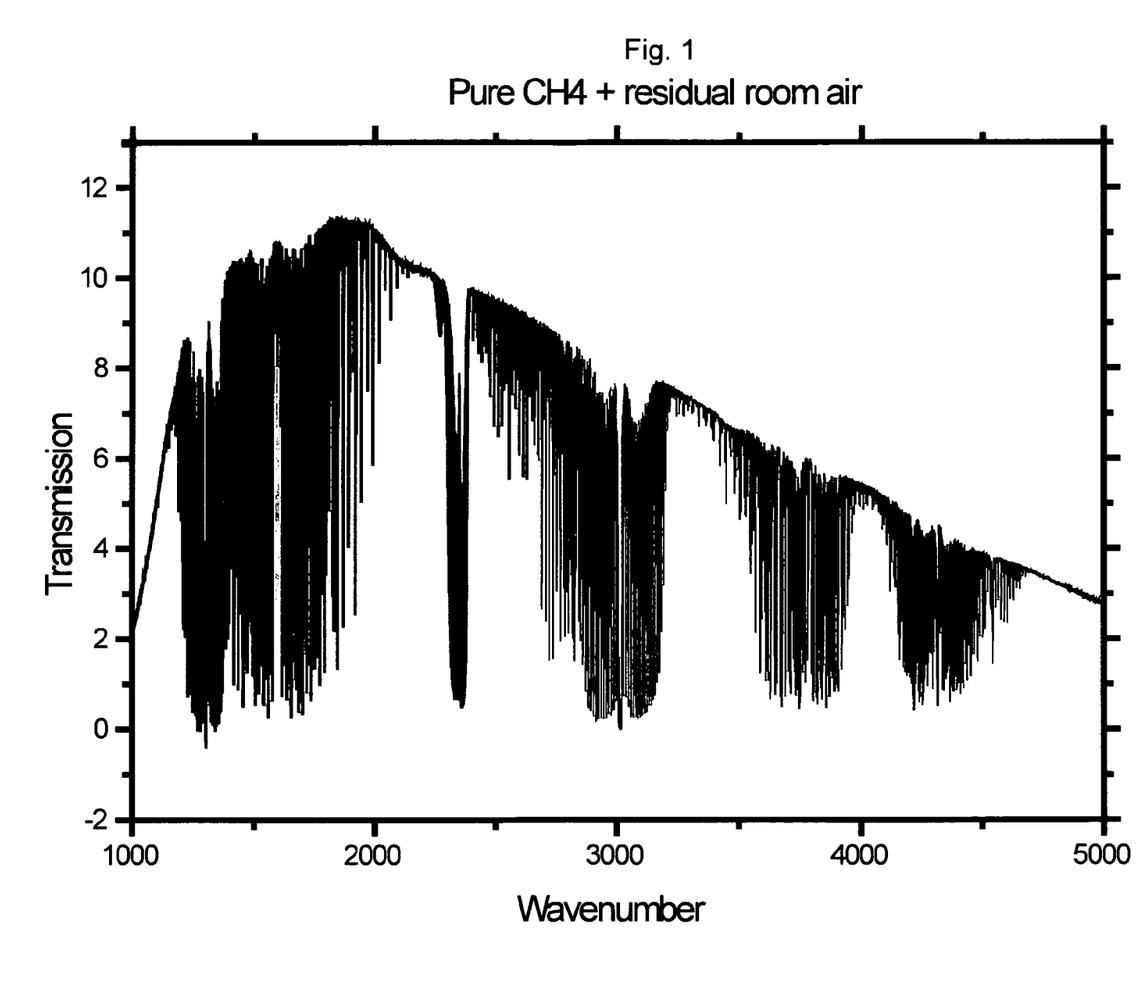
FIG. 1 illustrates a laboratory spectrum of a $CH_4$ and $H_2O$ mixture covering the range 1000 $cm^{-1}$ (10 microns) to 5000 $cm^{-1}$ (2 microns).

FIG. 1 shows a mid-infrared transmission spectrum of a $CH_4$ and $H_2O$ mixture covering the range 1000 $cm^{-1}$ (10 microns) to 5000 $cm^{-1}$ (2 microns) recorded using a Fourier Transform spectrometer. The individual "humps" (e.g., one is centered at 3000 $cm^{-1}$) are bands, and the many components of each band are lines. Some of these bands are due to $H_2O$ and others are due to $CH_4$. In many cases they overlap. Extensive examination of each region of this spectrum shows that the region near 1991.9 cm–1 is one of only two, and the highly preferred, spectral region where $H_2O$ can be distinguished from $CH_4$ over this wide wavelength range. The feature near 2350 wavenumber is residual $CO_2$ in room air, and some residual $H_2O$ absorption is also present. $H_2O$ in natural gas can only be measured in the "gap" regions where absorption by $CH_4$ is relatively weak.

Figure 2:
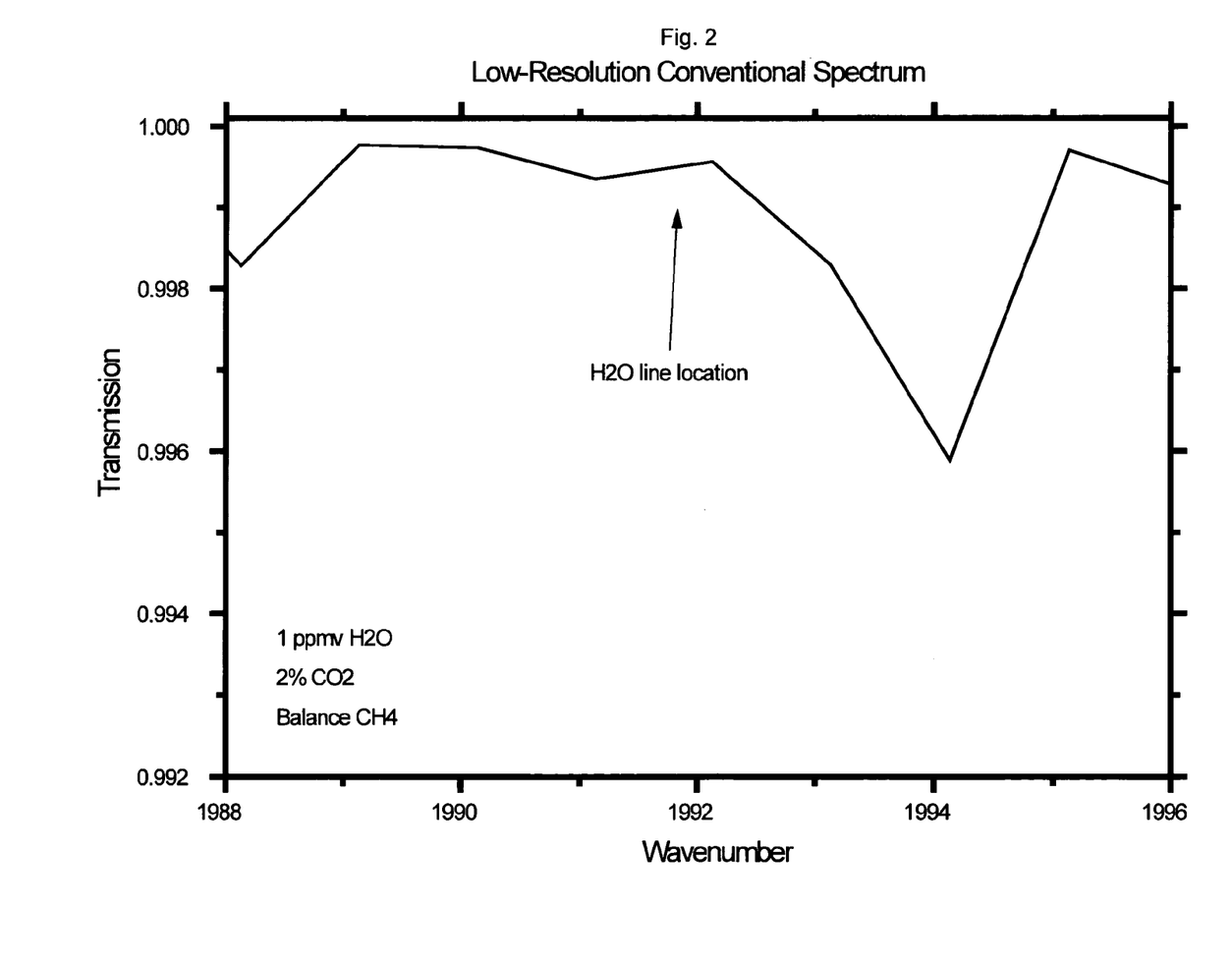
FIG. 2 is a detailed graph in the 1991.9 $cm^{-1}$ region for 1 ppmv $H_2O$ in a balance of pure $CH_4$ as the spectrum would appear if recorded with a conventional medium-resolution spectrometer.
Figure 3:
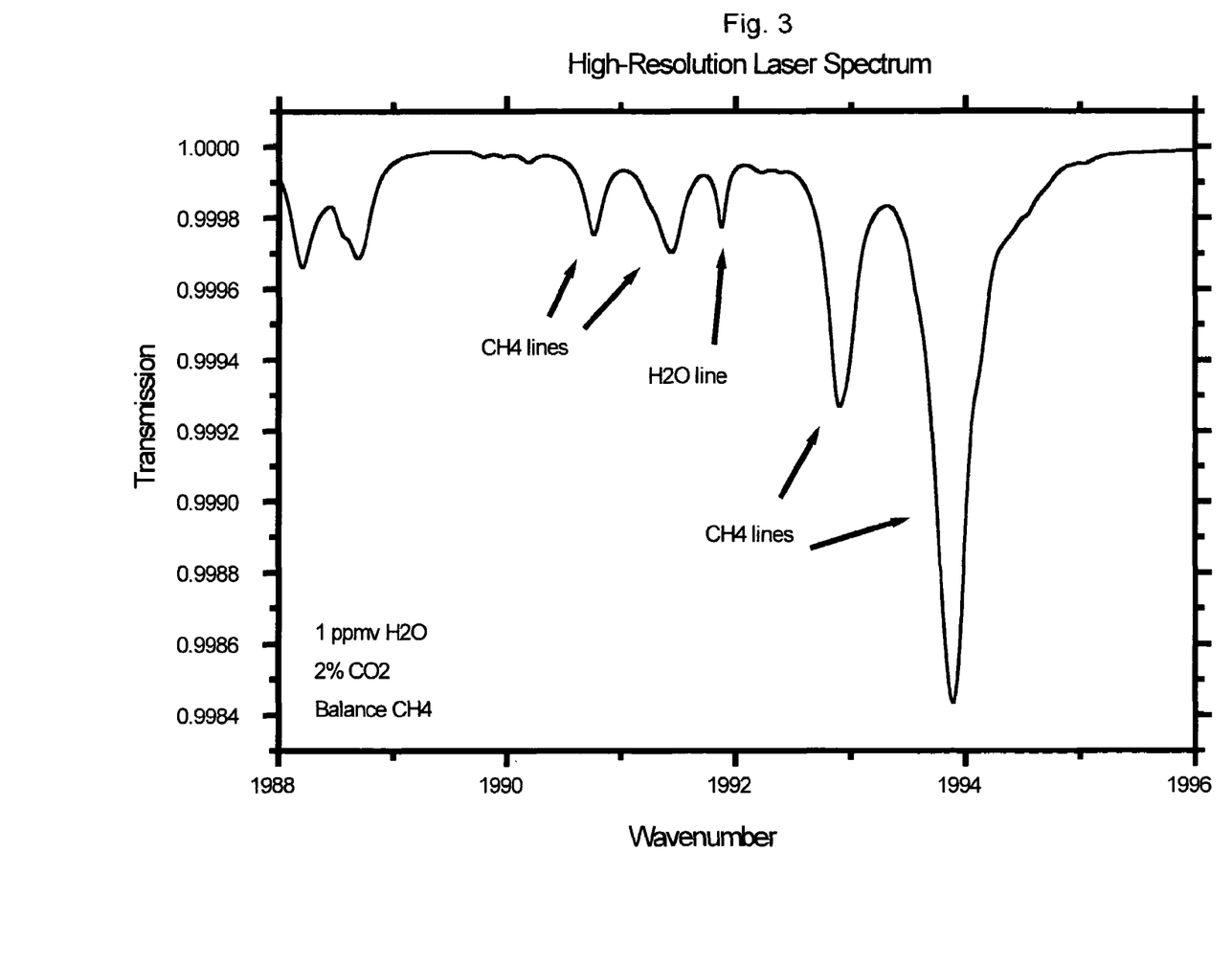
FIG. 3 is a detailed graph in the 1991.9 $cm^{-1}$ region for 1 ppmv $H_2O$ in a balance of pure $CH_4$ as the spectrum would appear if recorded using a high-resolution QC laser.

FIGS. 2 and 3 show detail in the 1991.9 $cm^{-1}$ region for 1 ppmv $H_2O$ in a balance of pure $CH_4$. FIG. 2 is a low-resolution graph of how the spectrum would appear if recorded with a conventional medium-resolution spectrometer. In this case, inadequate spectral resolution "blurs" the individual absorption lines due to the large instrumental distortion, and prevents the ability to measure $H_2O$ in natural gas.

In FIG. 3, high-resolution spectrum of the 1992 wavenumber spectral region showing the combined absorption from $CH_4$ with 2% $CO_2$ and 1 ppmv $H_2O$ as it would appear if recorded using a high-resolution QC laser. Here the $H_2O$ line can be clearly separated from the adjacent $CH_4$ lines, and as a result it is possible to measure $H_2O$ in natural gas using this wavelength at $H_2O$ concentrations down to approximately 0.1 ppmv, well below the tariff limits even in the coldest climates, and in ultra-dry process points such as the output of drying plants, or in liquified natural gas. It is the extremely high spectral resolution of a laser source that makes individual line separation possible.

Figure 4:
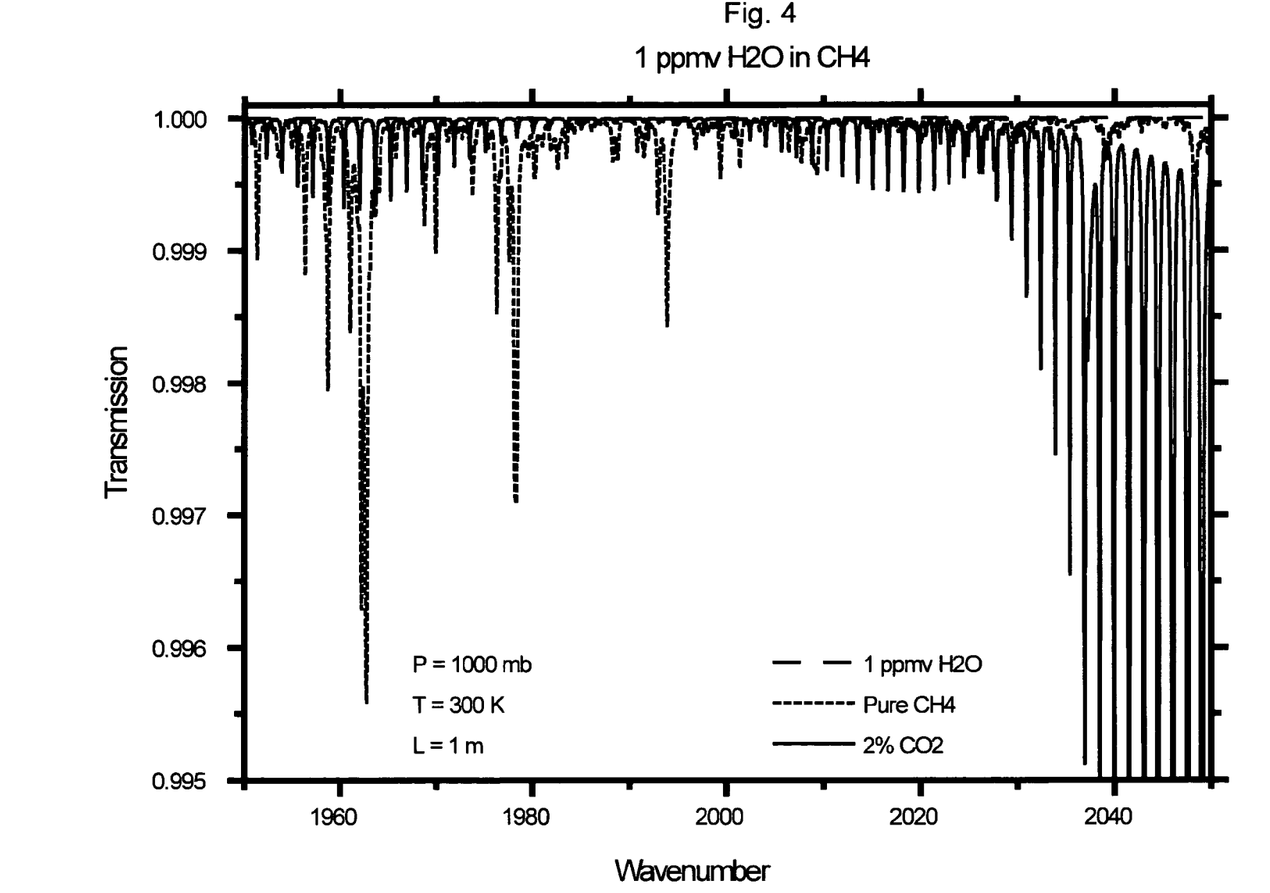
FIG. 4 is a graph of the transmission spectrum in the region 1950-2050 wavenumber (5.1282 to 4.8781 microns) where $CH_4$ absorption is relatively weak.

FIG. 4 illustrates the transmission spectrum in the region 1950-2050 wavenumber (5.1282 to 4.8781 microns) where $CH_4$ absorption is relatively weak. The strongest features here are due to $CO_2$ absorption, with weaker features from $CH_4$ and $H_2O$. Two individual $H_2O$ lines are located in this spectral region near 1967 wavenumber and 1992 wavenumber.

Figure 5:
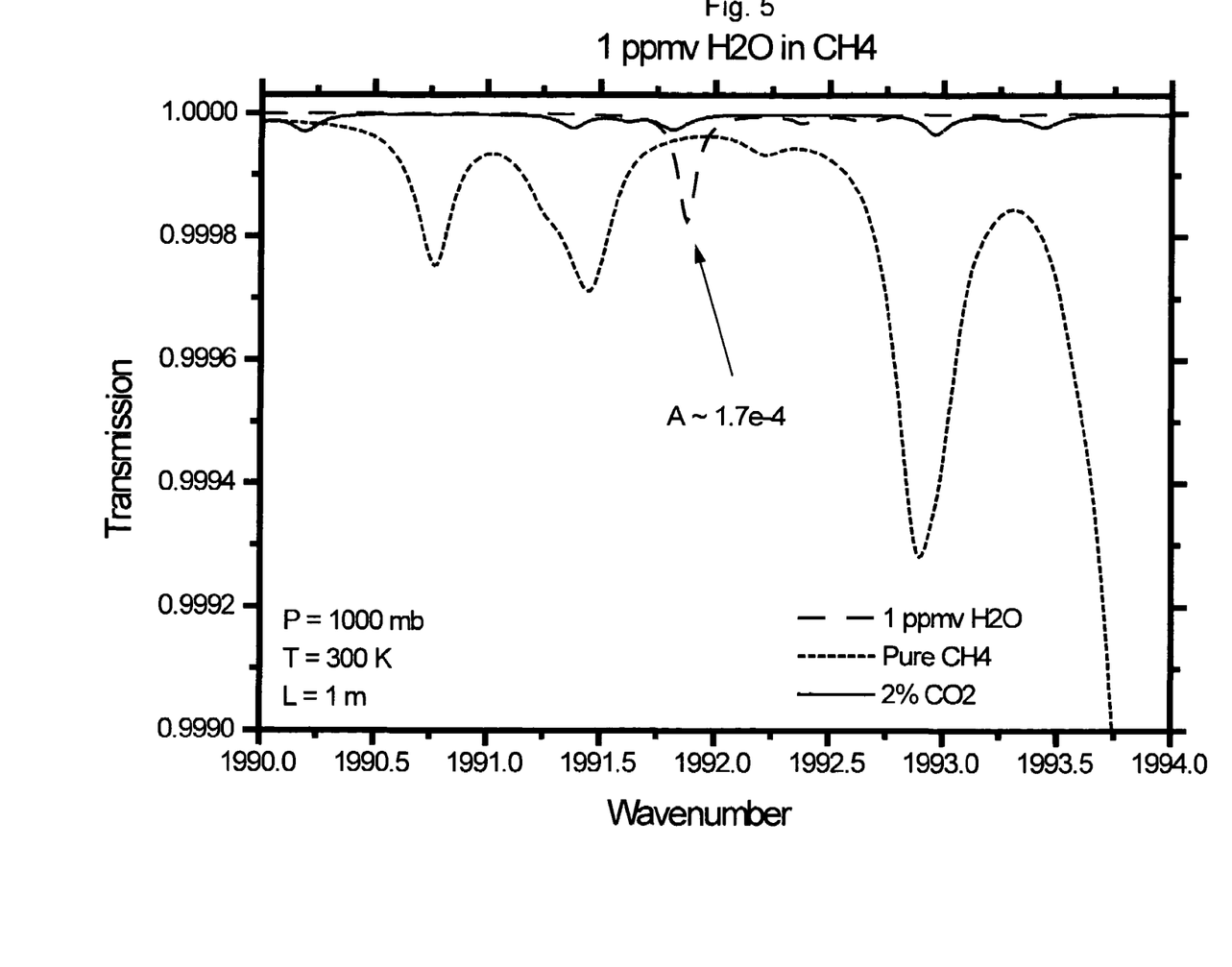
FIG. 5 is a graph of the expanded spectrum near 1992 wavenumber showing the best target $H_2O$ line for measurements of $H_2O$ in natural gas.

FIG. 5 is the expanded spectrum near 1992 wavenumber showing the best target $H_2O$ line for measurements of $H_2O$ in natural gas. This simulation is for a mixture containing primarily $CH_4$ with 2% $CO_2$ and I part per million by volume (ppmv) $H_2O$. The line center absorption for $H_2O$ at 1 ppmv concentration, environmental conditions shown (1000 mbar pressure ~1 atmosphere pressure, and 300 Kelvin ~27 Centigrade temperature), and a 1 meter optical absorption path is approximately $1.7 \times 10^{-4}$, or 0.017%. The arrow identifies the position of the target $H_2O$ line, which is relatively free of overlap by $CH_4$ (strongest features in the spectrum). $CO_2$ absorption is very weak in this region.

Figure 6:
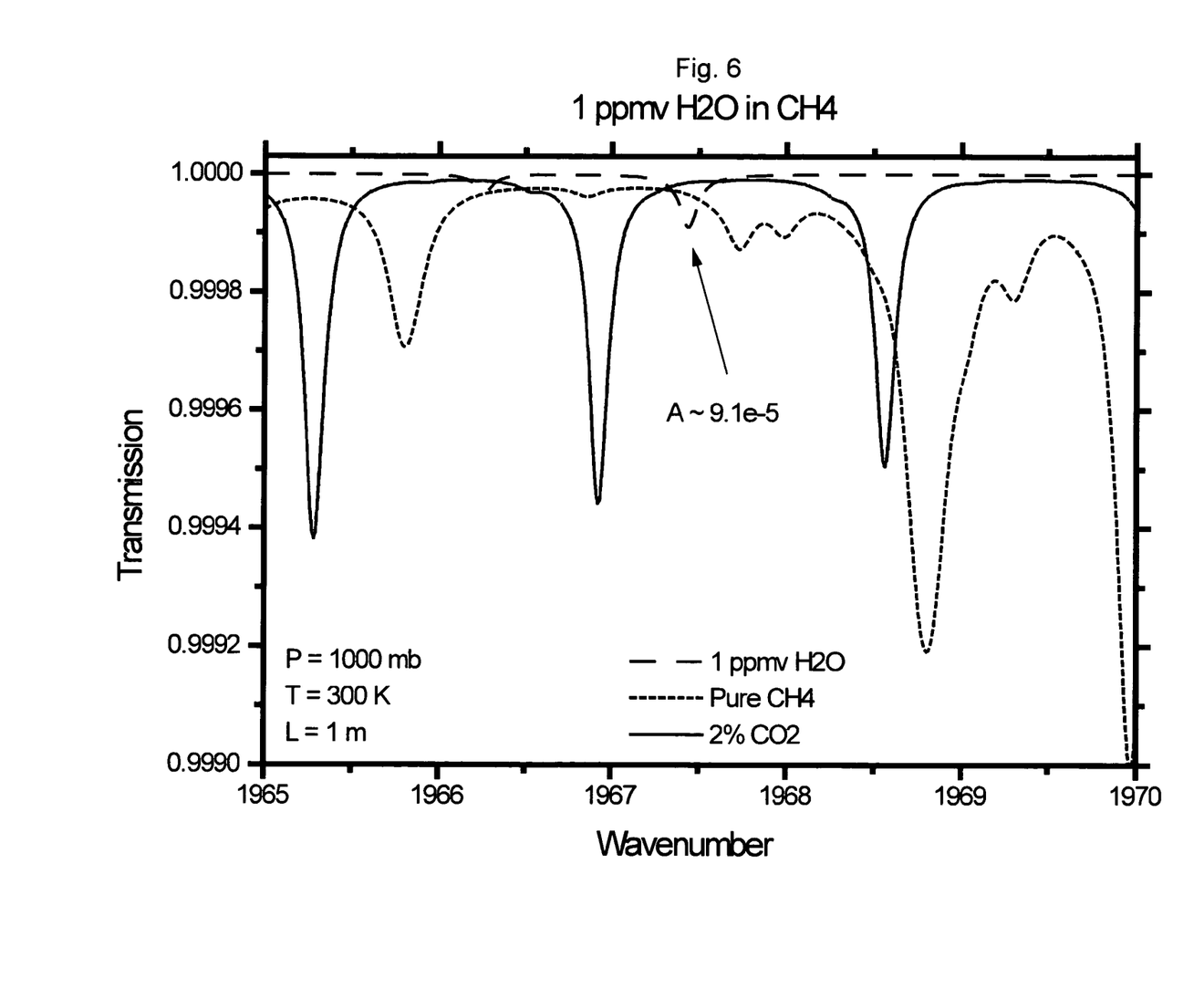
FIG. 6 is a graph of the spectrum for the region near the 1967 wavenumber.

FIG. 6 illustrates the spectrum for the region near 1967 wavenumber, i.e., 5.07 to 5.09 micron wavelength range, and in particular at the 5.08 microns wavelength, equal to 1967.5 $cm^{-1}$.

The $H_2O$ line here (indicated by the arrow) is weaker than the line at 1992 wavenumber, and is also more overlapped by $CH_4$ lines. This line can be used to measure $H_2O$ levels with reduced sensitivity, but is less desirable than the $H_2O$ line at 1992 wavenumber for measurement of $H_2O$ in natural gas.

Figure 7:
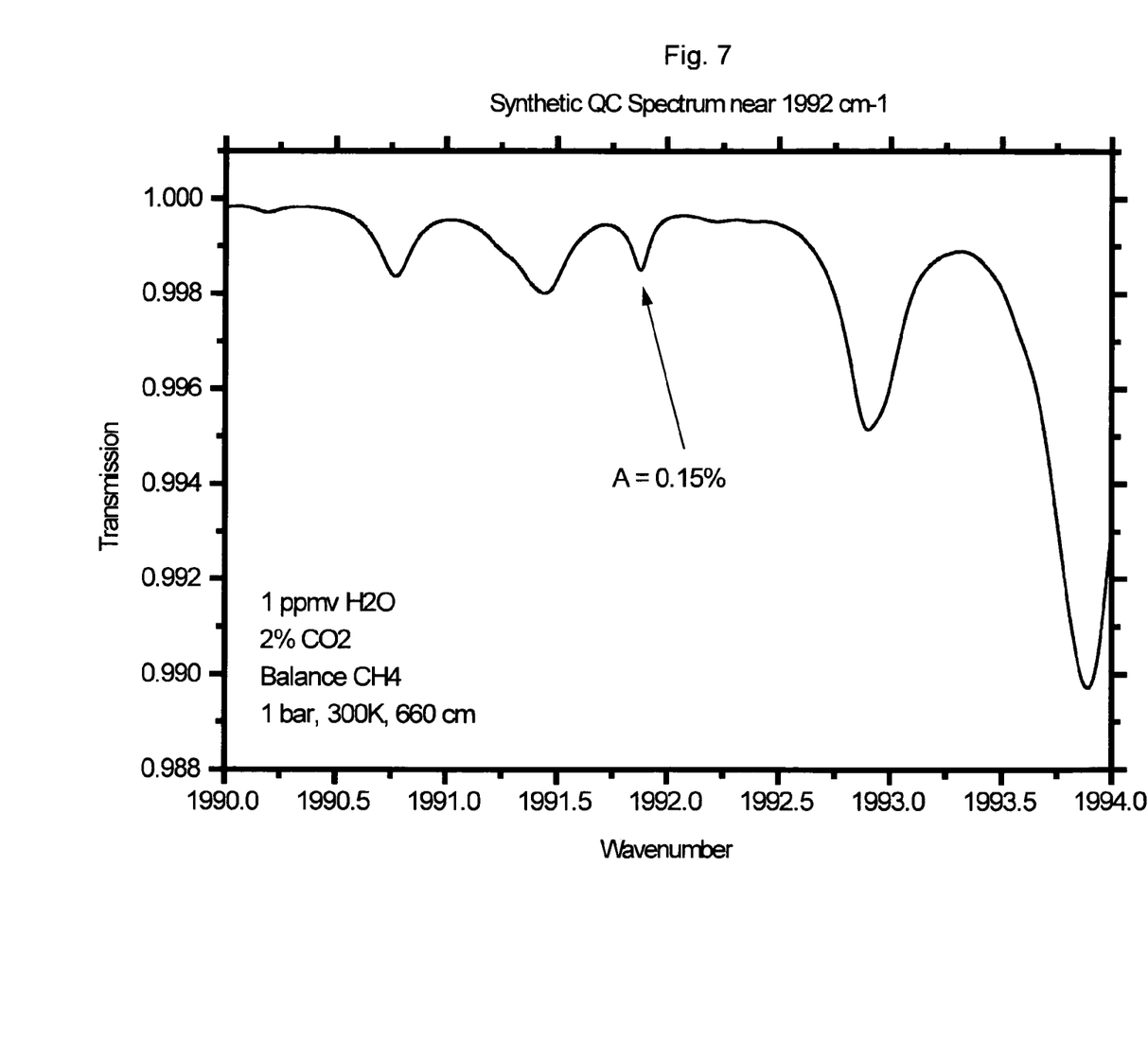
FIG. 7 is a graph of the composite spectrum of FIG. 5 generated for a 6.6 meter optical path length.

FIG. 7 shows the composite spectrum for the region near 1992 wavenumber where the individual absorptions from $CH_4$, $CO_2$ and $H_2O$ are summed. This is how the spectrum would appear if recorded with a QC laser. The optical pathlength is extended to 6.6 meters (compared to FIG. 5) which is ideal for measurements of $H_2O$ in natural gas down to 0.1 ppmv using direct absorption spectroscopy.

Figure 8:
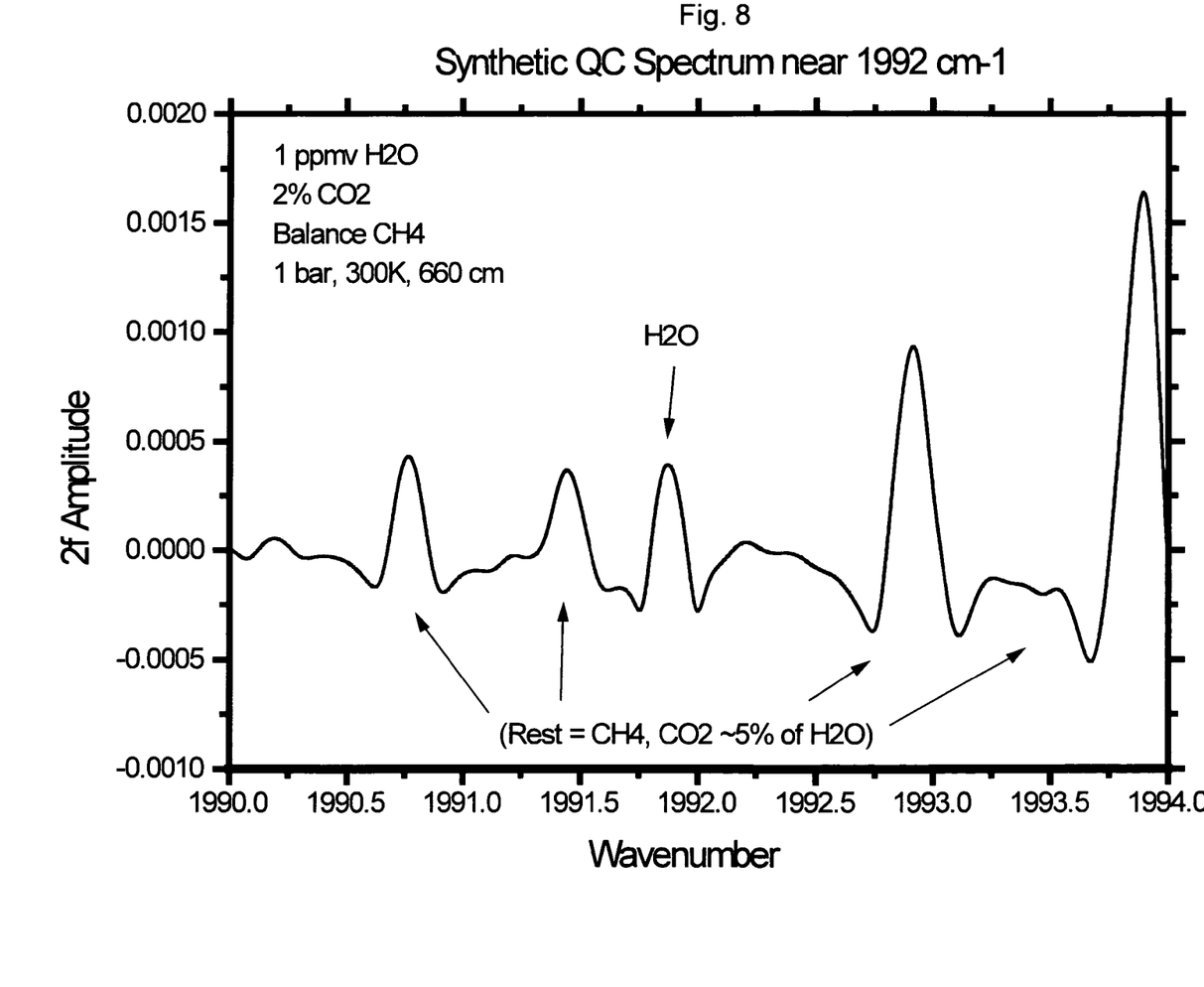
FIG. 8 is a graph of the second harmonic (2f) spectrum of the primary target $H_2O$ line at 1992 wavenumber.

FIG. 8 is the second harmonic (2f) spectrum of the primary target $H_2O$ line at 1992 wavenumber. The second harmonic detection technique is a common technique for gas measurements using tunable high-resolution lasers, and can provide typically 10-100 times greater sensitivity in comparison to direct transmission (all the spectra shown previously). It can also provide better separation and distinction of the target gas ($H_2O$ in this case) when the widths of the spectral features vary. With an optical path length of 660 cm (used for this example) the detection sensitivity for $H_2O$ in natural gas using 2f detection is below 0.1 ppmv, which is required for many applications in cold climates where the $H_2O$ tariff is low, and also at drying plants where water is initially removed from natural gas.

Figure 9:
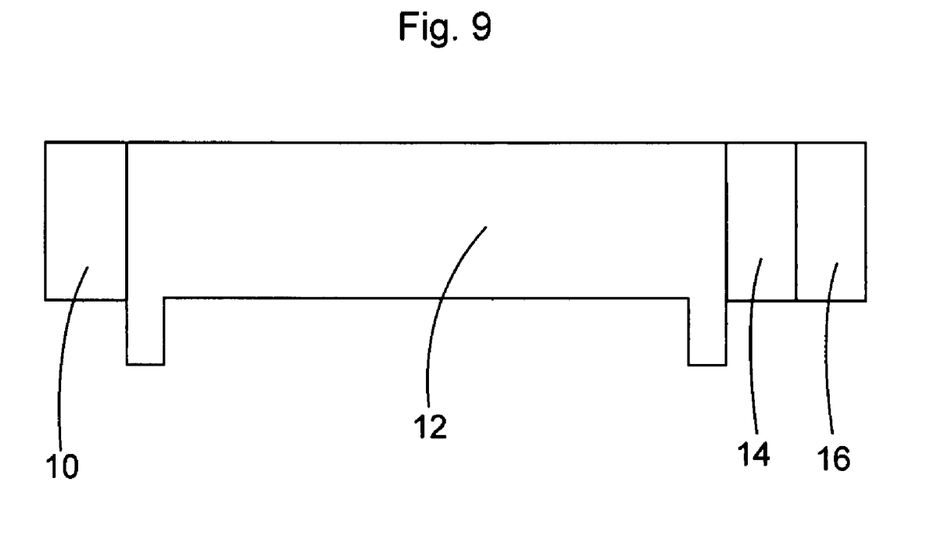
FIG. 9 is a schematic illustration of the system of the present invention.

As illustrated in FIG. 9, the present system for detecting water vapor in natural gas is comprised of a quantum cascade laser 10 positioned to emit light in the 5.01 to 5.03 micron, or the 5.07 to 5.09, wavelength range through a container 12, e.g., a pipe, filled with natural gas; a detector 14 configured to detect the intensity of light emitted; and an analyzer 16 coupled to the detector for determining the level of water vapor in the natural gas. The corresponding method is comprised of the steps of directing light in the 5.01 to 5.03 or the 5.07 to 5.09 micron wavelength range through natural gas; detecting the intensity of light transmitted through the natural gas; and determining the level of water vapor in the natural gas based on the light transmitted.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A system for determining the amount of water vapor in natural gas comprising: a light source for emitting light at a frequency in the 5.01 to 5.03 micron or the 5.07 to 50.9 micron wavelength range, and means for calculating the level of water vapor in natural gas from the intensity of light transmitted through said natural gas.

2. The system of claim 1 wherein said light source is a single-mode laser.

3. The system of claim 1 wherein said light source emits light at a wavelength of about 5.02 microns.

4. The system of claim 1 wherein said light source emits light at a wavelength of about 5.08 microns.

5. A system for detecting water vapor in natural gas comprising:
    a) a quantum cascade laser emitting light at a frequency in the 5.01 to 5.03 micron or the 5.07 to 5.09 micron wavelength range positioned to emit light through natural gas;
    b) a detector configured to detect the intensity of light transmitted through said natural gas from said laser; and
    c) an analyzer coupled to said detector for determining the level of water vapor in the natural gas.

6. The system of claim 5 wherein said laser emits light at a wavelength of about 5.02 microns.

7. A method for detecting water vapor in natural gas comprising: proving a light source for emitting light at a frequency in the 5.01 to 5.03 micron or the 5.07 to 5.09 micron wavelength range, directing light from said light source through natural gas containing water vapor, and calculating the level of water vapor in the natural gas from the intensity of light transmitted through said natural gas.

8. The system of claim 7 wherein said light source is a quantum cascade laser.

9. The system of claim 7 wherein said light source emits light at a wavelength of about 5.02 microns.

10. The system of claim 7 wherein said light source emits light at a wavelength of about 5.08 microns.

* * * * *